(12) United States Patent
Frayssinet et al.

(10) Patent No.: US 11,839,648 B2
(45) Date of Patent: Dec. 12, 2023

(54) AUTOLOGOUS CANCER VACCINES

(71) Applicant: Urodelia, Saiguede (FR)

(72) Inventors: Patrick Frayssinet, Saint Lys (FR); Nicole Rouquet, Toulouse (FR)

(73) Assignee: HASTIM, Toulouse (FR)

( * ) Notice: Subject to any disclaimer, the term of this patent is extended or adjusted under 35 U.S.C. 154(b) by 716 days.

(21) Appl. No.: 16/979,970

(22) PCT Filed: Mar. 13, 2019

(86) PCT No.: PCT/FR2019/050537
§ 371 (c)(1),
(2) Date: Sep. 11, 2020

(87) PCT Pub. No.: WO2019/175500
PCT Pub. Date: Sep. 19, 2019

(65) Prior Publication Data
US 2021/0008187 A1   Jan. 14, 2021

(30) Foreign Application Priority Data
Mar. 14, 2018 (FR) ...................................... 1852197

(51) Int. Cl.
*A61K 39/00* (2006.01)
*A61K 9/00* (2006.01)
*A61K 39/395* (2006.01)
*C01B 25/32* (2006.01)

(52) U.S. Cl.
CPC ........ *A61K 39/0011* (2013.01); *A61K 9/0019* (2013.01); *A61K 39/39516* (2013.01); *C01B 25/32* (2013.01)

(58) Field of Classification Search
CPC .............. A61K 39/0011; A61K 9/0019; A61K 39/39516; A61K 2039/55505; A61K 2039/60; C01B 25/32; A61P 35/00
See application file for complete search history.

(56) References Cited

U.S. PATENT DOCUMENTS 5,051,355 A    9/1991  Yoshida et al.

FOREIGN PATENT DOCUMENTS

| EP | 2564867 A1 | 3/2013 |
|----|------------|--------|
| JP | S63-21562 A | 1/1988 |
| JP | S63-41427 A | 2/1988 |
| WO | 2006/122914 A2 | 11/2006 |
| WO | 2014/184453 A1 | 11/2014 |

OTHER PUBLICATIONS

Kierkegaard et al., "Predictive and Prognostic Values of Cancer-Associated Serum Antigen (CASA) and Cancer Antigen 125 (CA 125) Levels Prior to Second-Look Laparotomy for Ovarian Cancer," Gynecologic Oncology, 59: 251-254 (1995).

(Continued)

*Primary Examiner* — Trevor Love
(74) *Attorney, Agent, or Firm* — Morgan, Lewis & Bockius LLP

(57) ABSTRACT

The invention relates to an autologous cancer vaccine and also to the method for producing same comprising the following steps: a) extracting the proteins contained in a serum or plasma sample obtained from a patient suffering from cancer; and b) bringing the proteins extracted in step a) into contact with particles of hydroxyapatite and/or tricalcium phosphate.

7 Claims, 2 Drawing Sheets

(56) References Cited

OTHER PUBLICATIONS

International Search Report issued in corresponding International Patent Application No. PCT/FR2019/050537 dated Jun. 12, 2019.
Marconato et al., "Enhanced therapeutic effect of APAVAC immunotherapy in combination with dose-intense chemotherapy in dogs with advanced indolent B-cell lymphoma," Vaccine, 33: 5080-5086 (2015).
Marconato et al., "Randomized, Placebo-Controlled, Double-Blinded Chemoimmunotherapy Clinical Trial in a Pet Dog Model of Diffuse Large B-cell Lymphoma," Clinical Cancer Research, 20: 668-677 (2013).
Ciocca et al., "A pilot study with a therapeutic vaccine based on hydroxyapatite ceramic particles and self-antigens in cancer patients," Cell Stress and Chaperones, 12: 33-43 (2007).
Srivastava, "Immunotherapy of Human Cancer: Lessons from Mice," Nature Immunology, 1: 363-366 (2000).
Rossi et al., "Apavac, a Simple Autologous Vaccination Process (AV) Associated with Clinical Efficacy in 56 Patients (pts) Having Cancer (C) and 11 Pts Having Hematological Malignancies (HM)," Blood, 132: 5690 (2018).

AUTOLOGOUS CANCER VACCINES

TECHNICAL FIELD OF THE INVENTION

The present invention relates to the treatment of cancer by immunotherapy. The present invention relates in particular to the production of autologous cancer vaccines.

TECHNOLOGICAL BACKGROUND

Immunotherapy is a recognized and well-established therapeutic alternative for treating cancer. It groups together several different therapies, all based on stimulating the immune system of the patient in order to recognize and attack his or her disease.

The cells of the immune system are normally capable of monitoring and detecting the presence of abnormalities within the cells of the body. However, most tumors develop several mechanisms in order to escape this monitoring; tolerance of the immune system toward the tumor is then observed. Stimulating the immune cells, such as the T lymphocytes, so that they specifically recognize the tumor cells makes it possible to lift this tolerance.

This stimulation can, for example, be carried out by directly bringing the tumor antigens into contact (in vitro or in vivo) with the macrophages or related cells so that the antigen-presenting cells (APCs) stimulate the T lymphocytes. This is the concept of a therapeutic cancer vaccine. For an in vivo stimulation, the principle is to remove abnormal proteins from the tumor and to reinject them in a form that is visible to the immune system.

Therapeutic cancer vaccines can be based on the use of heat shock proteins (HSPs) such as gp 96, or HSP 70. These proteins are chaperone molecules and associate with numerous peptides including the antigens specific for the tumor of each patient. They thus constitute a molecular fingerprint of the tumor to be eradicated and differ from one patient to another and from one tumor to the other. For the same tumor, said fingerprint evolves over time.

This vaccination strategy makes it obligatory to purify the vaccinating proteins from each tumor against which they must immunize the patient and at a given time. The purification protocol is lengthy, difficult to industrialize and subject to multiple contaminations by endotoxins. It is conventional to purify HSPs from ground tumor material which is subjected to a series of centrifugation, precipitation, chromatography on Con A, electrophoretic analysis, and chromatography on Mono Q FPLC. U.S. Pat. Nos. 6,447,781, 6,436,404, 6,410,028, 6,383,494 and 6,030,618 describe methods for purifying HSP proteins, consisting in using Con A Sepharose chromatographic columns.

Patent application WO 2006/122914 has described the usefulness of employing hydroxyapatite (HAP) particles for purifying the vaccinating proteins from tissue extracts. This application describes more particularly a single-step method for producing tumor antigens, intended to place them in a form recognizable by the immune system in order to be able to apply it on a large scale by personnel who are not a qualified biochemist. WO 2006/122914 also indicates that the HAP powders and also powders of other calcium salts can be used as vaccination adjuvants and that the hydroxyapatite powder that has adsorbed the tumor-specific tumor antigens can be used as a medicament against said tumor. Thus, the same HAP powder can be used both to purify the proteins specific for a tumor and to stimulate the immune system against said proteins when powders and proteins are injected together.

The development of an improved method for producing a powder of hydroxyapatite and/or tricalcium phosphate has also been described in patent application WO 2014/184453. The powder thus obtained is brought into contact with tumor proteins directly purified from tumor biopsies, and therefore marking the cellular identity of the tumor, in order to produce a therapeutic antitumor vaccine which increases the level of innate immunity without additional toxicity or side effect.

This technique is safe, can be combined with chemotherapy and produces no toxic residue. The inventors demonstrated that the T lymphocytes were capable of recognizing the tumor cells after vaccination. The vaccination cycle is very similar to that used for anti-infectious vaccine. The vaccine is injected into the subcutaneous tissue and several injections are required (one a week for 4 weeks and one a month for 4 months).

This type of immunotherapy can make the difference between remission and recovery from certain cancers with a poor prognosis. This has for example been demonstrated in veterinary medicine, where this vaccination increases the survival of dogs compared to chemotherapy alone for a deadly cancer such as high-grade B lymphomas (DLBCL). Excellent results have also been obtained for solid tumors such as bone cancers (osteosarcomas), mastocytomas or else melanomas.

However, the production of these vaccines from biopsies has several difficulties which considerably impair an industrial use. The first of these difficulties is the necessary biopsy of the tumor in an area which is not necrotic and which is representative of the antigenic level of the entire tumor and any possible metastases from said tumor.

Furthermore, it may not always be possible to obtain the biopsies, in particular if they represent by themselves a vital risk or a risk of significant after-effects in individuals for whom there is a high anesthetic risk because of multiple and damaging pathological conditions. This risk is particularly high for tumors such as pancreatic adenocarcinomas or brain tumors that are difficult to access or even high-grade prostate tumors because of the risks of dissemination.

In addition, from a regulatory point of view, the management of biopsies is a laborious and complicated affair. It requires creating a tissue bank, following strict regulations, carrying out monitoring of the cold chain and undertaking complex logistics.

The cost of a biopsy and of the management of the latter in a tissue bank can therefore easily be greater than that of the treatment per se.

It would therefore be extremely advantageous and beneficial to be able to develop a cancer vaccine which can be produced without recourse to tumor biopsies while at the same time preserving an efficacy comparable to vaccines produced from tumors.

BRIEF DESCRIPTION OF THE INVENTION

Surprisingly, the present inventors have managed to develop a cancer vaccine which gives results that are comparable, or even superior, to those obtained with the vaccine described in application WO 2014/184453 (based on proteins from tumor biopsies and HAP particles), but this being without recourse to a tumor biopsy.

The present inventors have in fact realized that it is possible to develop such a vaccine by directly extracting the tumor proteins from the blood, and in particular from the serum, of an individual suffering from cancer.

In this context, the present invention relates to a method for producing an autologous cancer vaccine, said method comprising the following steps:
a) extracting the proteins contained in a serum or plasma sample obtained from a patient suffering from cancer; and
b) bringing the proteins extracted in step a) into contact with particles of hydroxyapatite and/or of tricalcium phosphate.

The present invention also relates to the autologous vaccine obtained from the production method mentioned above.

Finally, the present invention also relates to the autologous vaccine obtained from the production method mentioned above, for use thereof in therapy, and particularly in the treatment of cancer in the patient from whom the serum and/or plasma sample was obtained (autologous vaccine).

DETAILED DESCRIPTION OF THE INVENTION

The present inventors have demonstrated that it is possible to develop an efficacious cancer vaccine based on hydroxyapatite particles exhibiting tumor antigens, said tumor antigens having been obtained, not from tumor biopsies as was the case in the prior art, but from plasma or serum samples from the patient.

In a first aspect, the present invention thus relates to a method for producing a cancer vaccine, and particularly an autologous cancer vaccine, said production method comprising the following steps:
a) extracting the proteins contained in a serum or plasma sample obtained from a patient suffering from cancer; and
b) bringing the proteins extracted in step a) into contact with particles of hydroxyapatite and/or of tricalcium phosphate.

An "autologous" vaccine denotes a vaccine in which the tumor proteins/antigens are obtained from the patient intended to be vaccinated.

The "patient" or "subject" is a human being or an animal, for example a mammal, and in particular dogs, horses or cats.

A serum or plasma sample is typically obtained from a blood sample taken from the patient to be treated. The blood is subjected to centrifugation in order to separate the heaviest components from the supernatant. This supernatant constitutes the plasma if it involves anti-coagulated blood or the serum if the blood has coagulated naturally.

The notion of "tumor proteins/antigens" is well known to those skilled in the art. They are proteins and/or molecules expressed specifically by the tumor cells and which can be recognized by T and B lymphocytes.

According to the present invention, the tumor proteins/antigens are directly extracted from the serum or plasma sample obtained from the patient to be treated. Typically, the weight of the tumor proteins/antigens extracted from the serum or plasma sample is between 60 kDa and 130 kDa, in particular between 70 kDa and 110 kDa.

Those skilled in the art are aware of a large number of techniques for extracting proteins from a serum or plasma sample. Typically, the tumor proteins/antigens are extracted by precipitating the serum sample in a saline solution, the mixture thus obtained is then centrifuged, and the pellet obtained represents the extracted proteins.

In one particular embodiment, all of the proteins/antigens extracted from the plasma/serum are used and brought into contact in order to produce the vaccine according to the present invention. That is to say that the whole of the "pellet" of proteins/antigens extracted from the plasma/serum is brought into contact with the hydroxyapatite particles.

"Hydroxyapatite" is a mineral of the calcium phosphate family, of formula $Ca_{10}(PO4)_6(OH)_2$, and the unit cell of the crystalline structure is hexagonal. Hydroxyapatite is the hydroxylated member of the apatite group. The ions of the crystal unit cell can be replaced with other ions of similar charges and sizes; tunnels also exist in the unit cell which can receive small molecules such as certain amino acids. These are those particular features which give this mineral very specific adsorption properties.

The hydroxyapatite particles according to the present invention are obtained via the same method as that described in application WO 2014/184453, the content of which is incorporated herein by way of reference. This document describes in particular a method for producing calcium phosphate hydroxyapatite $Ca_{10}(PO4)_6(OH)_2$ particles, consisting of a slow precipitation at high temperature, obtained by double decomposition of a calcium salt and of a phosphorus salt in a basic medium. The reaction is carried out at constant temperature in a large reaction volume and is followed by a maturation phase and a phase of washing with water. The precipitate thus obtained undergoes a further transformation step: solid/solution separation. The latter step is carried out either by filtration, drying by stoving and crushing, or by spray-drying using a fluidized bed. Regardless of the solid/solution separation technique chosen, the powder will undergo two transformation steps specific to the application of the invention: the step of particle size selection by dry screening so as to retain only the particle size band of interest, less than 25 μm or between 25 and 45 μm, then a final step during which the powder will be sintered at an optimal temperature to ensure fusion of the grains resulting in quite particular surface finishes of the powders (preferentially greater than or equal to 30 $m^2$/g). These two final steps can be reversed: selection then sintering or sintering then selection. "Sintering" is a process consisting in heating a powder without bringing it to melting. In the context of the present invention, the sintering is for example carried out at a temperature between 400° C. and 600° C. The HAP thus obtained may be in powder form and may undergo one or more washes.

Typically, the tumor proteins/antigens are brought into contact with hydroxyapatite particles by passing said tumor proteins/antigens over a column of hydroxyapatite particles, such as a chromatography column. The tumor antigens may optionally be brought into contact in solution and then washed by centrifugation. The tumor proteins/antigens are then adsorbed onto the surface of the hydroxyapatite particles. The hydroxyapatite particles may particularly be in powder form.

When a chromatography column is used, it can for example be placed under pressure.

Once the hydroxyapatite particles have been loaded with tumor proteins/antigens, they are suspended in an injection liquid and injected into the patient from whom the serum/plasma sample was obtained.

Typically, the injection liquid comprises an organic agent which facilitates the injection, such as carboxymethylcellulose.

One aspect of the invention relates to an autologous vaccine comprising particles of hydroxyapatite and/or of tricalcium phosphate which are loaded with tumor antigens obtained from a serum or plasma sample from a patient suffering from a cancer.

Typically, the autologous vaccine is in the form of a suspension.

Typically, the weight of the tumor antigens extracted from the serum or plasma sample is between 60 kDa and 130 kDa, in particular between 70 kDa and 110 kDa.

According to one particular embodiment, the autologous vaccine is obtained according to the method described above.

The autologous vaccine according to the present invention thus comprises the particles of HAP and/or of tricalcium phosphate that have adsorbed the patient-specific tumor antigens (obtained from a serum or plasma sample from said patient) and that have been resuspended.

This vaccine is then preferably administered by injection, for example by subcutaneous or intradermal injection. The vaccine can be administered orally or by any other means allowing transmucosal vaccination.

The present invention also relates to the use of the autologous vaccine obtained according to the method above, for use thereof in therapy, and particularly in the treatment of cancer in the patient from whom the tumor proteins/antigens were obtained.

Another aspect of the invention also relates to a method for treating a patient suffering from a cancer, said method comprising the following steps:

a) extracting proteins contained in a serum or plasma sample obtained from a patient suffering from cancer;
b) bringing the proteins extracted in step a) into contact with particles of hydroxyapatite and/or of tricalcium phosphate;
c) suspending, in an injection liquid, the particles of hydroxyapatite and/or of tricalcium phosphate brought into contact with the proteins in step b);
d) injecting the mixture obtained in step c) into the patient from whom the serum or plasma sample used in step a) was obtained.

In the context of the present invention, the "cancer" may be any cancer for which immunotherapy may be indicated. The cancer may particularly be chosen from a nonexhaustive list comprising melanomas, carcinomas or adenocarcinomas which develop from epithelial cells and/or cells from a gland, sarcomas which develop from connective or muscle tissue cells, central nervous system tumors, hematopoietic system tumors such as leukemias, and lymphomas. The various cancers of infectious origin, the most representative of which are cervical cancers, primary liver cancer and gastric cancers, may also be included.

In one particular embodiment, the cancer is chosen from the group consisting of osteosarcomas, B or T lymphomas, mammary tumors, melanomas, hemangio sarcomas, mastocytomas, fibrosarcomas, brain or central nervous system tumors, schwannomas, mesotheliomas, seminomas, teratomas and blastomas.

In one preferred embodiment, the cancer is chosen from a glioblastoma, a sarcoma (such as osteosarcoma or fibrosarcoma), a melanoma, a carcinoma or an adenocarcinoma.

In one particular embodiment, the cancer is a disseminated cancer, that is to say one which has metastases (patients classified in the NxMx category according to the TNM classification).

The patient may receive one or more injections, doses of vaccine. A dose generally comprises between 30 and 50 mg of hydroxyapatite and/or of tricalcium phosphate and between 1000 and 2000 μg of proteins.

Preferably, the patient may receive several injections spaced out over time, for example several days, weeks or months. In one preferred embodiment, the injections are separated by a week during the first month and then by a month for 4 months.

Each injection can be ideally prepared from a new sample of tumor proteins from the patient in the event of escape from the vaccine or of inefficacy in particular when there is an increase in the level of tumor markers.

The present vaccine represents a considerable evolution of the protocol compared with the technique using tumor biopsies: the proteins do not need to be extracted from the intracytoplasmic sector.

The SDS Page electrophoreses of the proteins attached to the powders ready to be injected show that the protein bands are different from those obtained by tumor biopsy (as in application WO 2014/184453). Furthermore, as demonstrated hereinafter, the results obtained with a vaccine according to the present invention are as good, or even better.

The autologous vaccine according to the present invention can be used in combination with another anticancer treatment, such as radiotherapy, chemotherapy or another immunotherapeutic agent.

The present invention is presented in greater detail in the examples below. These examples are provided only for illustrative purposes and cannot be interpreted as limiting the scope of the present invention.

EXAMPLES

Figure 1:
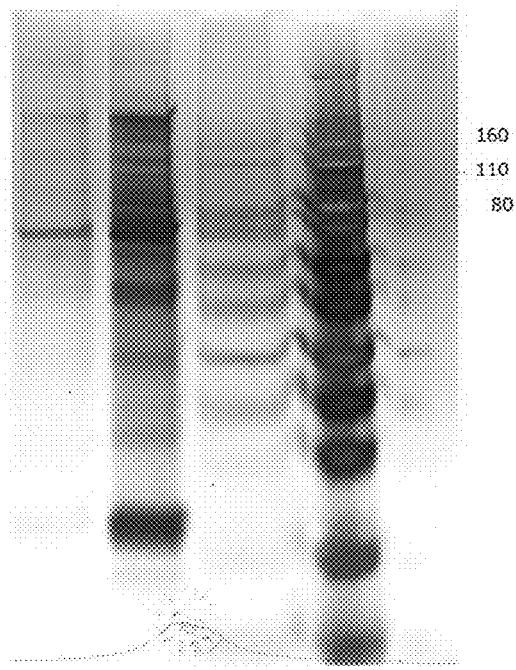
FIG. 1: SDS Page of proteins detached from the surface of the powder of vaccines produced from various tumors. From left to right: mammary adenocarcinoma, diffuse lymphoma, and osteosarcoma. The results are both qualitatively and quantitatively variable. Scale in kDa.
Figure 2:
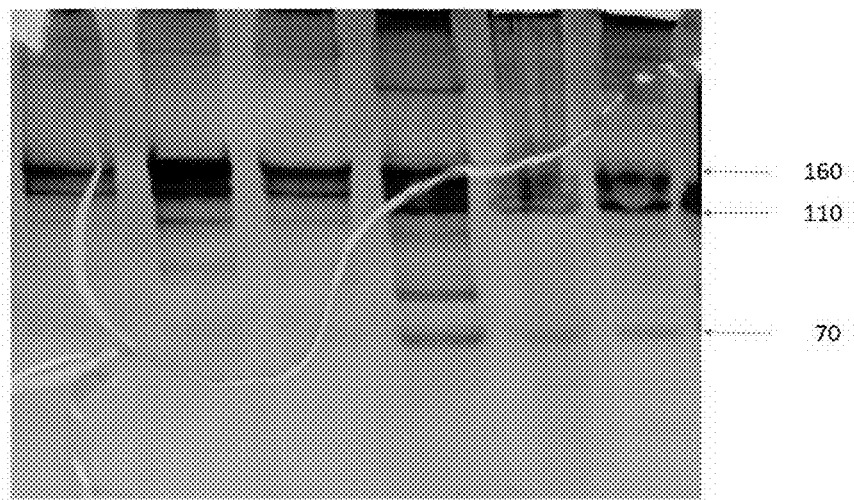
FIG. 2: SDS Page of proteins obtained from vaccines prepared from serum. From left to right, melanoma (first two columns), tongue cancer (next 2), hemangiosarcoma (next 2). Scale in kDa. There are many fewer contaminations; the main bands quantitatively are between 160 and 110 kDa. This is very reproducible.

The present protocol was carried out in patients exhibiting pathological conditions with very poor prognosis, that are incurable using the therapies used at the time. The patients participated in the present protocol by making an express request to do so and by signing an informed consent.

The present protocol may be indicated for disseminated cancers as last-line treatment after the failure of conventional therapies, optionally combined with chemotherapy or another immunotherapy. The prevention of recurrences for cancers without efficacious therapy after surgery may also be envisioned.

Twenty-seven patients were included in this protocol. Nine patients were subjected to the immunotherapy protocol without any added chemotherapy treatment. 10 patients had a glioblastoma, 2 had a sarcoma and 15 had a carcinoma or an adenocarcinoma. 22 patients had an evolutive disease at the time the immunotherapy protocol was applied, 13 of these patients were free of disease or had a stable disease or a partial regression 5 months after the beginning of the protocol. When the glioblastomas were set aside, 72% of the patients who were suffering from evolutive disease at the time of the vaccination moved, two months after the vaccination, into a stable state (SD) or into partial regression (PR). In the conclusions, although this series is heterogeneous, a significant percentage of cases showed a clinical response to this last-line technique and no side effect occurred. Disseminated cancers can be stabilized by this technique, showing that the immune response can be obtained in human beings, even for a rapid advanced and evolutive disease.

Example 1: Difference Between the Electrophoresis of the Proteins Adsorbed onto the Powders in Contact with the Serum or with a Tumor Biopsy The electrophoreses of the proteins contained in the vaccines prepared from a biopsy or else from the serum proteins were compared.

The HAP particles were typically obtained according to the method described in Example 1 of application WO 2014/184453.

The Doses were Prepared as Follows:

Starting from a Biopsy:

The tumor tissue and all the materials used to prepare the vaccine were handled sterilely in a laminar flow hood. The frozen tumor tissue (200 mg) was homogenized using a tissue ball homogenizer. 1 ml of $NaHCO_3$ (30 mM, pH 7) was added per 1 ml of homogenate.

The resulting homogenate was then centrifuged at 1000 g for 15 min at 4° C. in order to remove all the tissue debris. The supernatant is mixed at 50% in a solution supersaturated with aqueous ammonium nitrate and placed at 4° C. for one hour and then centrifuged. The pellet is resuspended in a 0.02 M phosphate buffer, pH 7. This solution is then percolated in a chromatography column containing the HAP powder. The column was filled (Poly-prep chromatography columns, Cat.731-1550, Bio Rad) with 0.2 g of HAP (0-25 µm), equilibrated with 10 volumes of phosphate buffer (20 mM, pH 7). The resuspended pellet was then added. The column was then washed with 3 ml of a 100 mM NaCl solution. The powder was then suspended in 5 ml of carboxymethylcellulose (CMC) solution (2% in 20 mM NaCl). 0.5 ml of this solution was added for each vaccine injection.

Starting from Serum:

The procedure is much simpler, 3 cc of serum are diluted to 50% in a supersaturated aqueous ammonium nitrate solution, placed at 4° C. for one hour and then centrifuged. The pellet is resuspended in a 0.02 M phosphate buffer, pH 7. This solution is then percolated in a chromatography column containing the HAP powder. The column was filled (Poly-prep chromatography columns, Cat.731-1550, Bio Rad) with 0.2 g of HAP (0-25 µm), equilibrated with 10 volumes of phosphate buffer (20 mM, pH 7). The resuspended pellet was then added. The column was then washed with 3 ml of a 100 mM NaCl solution. The powder was then suspended in 5 ml of carboxymethylcellulose (CMC) solution (2% in 20 mM NaCl). 0.5 ml of this solution was used for each vaccine injection.

In the two cases for the electrophoresis, the proteins adsorbed onto the powders are desorbed before the electrophoresis. 10 mg of powders of a vaccine dose are centrifuged for two minutes at 500 g. The supernatant is removed and the pellet is resuspended in 0.5 ml of 0.5 M NaCl. The powders are stirred, resuspended and centrifuged at 500 g.

10 µl of the supernatant liquid are then placed in the electrophoresis wells, after having been diluted to 50% in detergent and heated at 70° C. for 5 min.

Results:

There are notable differences between the electrophoretic profiles obtained with the two methods. The most striking are a decrease in the number of bands on the electrophoreses originating from the blood, compared with that originating from biopsies (FIG. 1, 2). The electrophoreses originating from the blood are also much more homogeneous, showing a better reproducibility of the purification.

Example 2: Results of the Administration of the Vaccine According to the Invention in a Patient Suffering from Adenocarcinoma This patient presented an endometrial adenocarcinoma (TNM 7a) treated pre- and post-operatively with two cycles of paclitaxel and of carboplatin. 18 months after the patient showed a pulmonary miliaria and secondary localizations on retroperitoneal sites, she received hormone treatment (megestrol acetate) and began the vaccines. At three months (MRI, PET) after vaccination, she showed a stabilization of her pulmonary pathology and a slight regression of the volume of the retroperitoneal masses, which then continued, since, at 18 months, the retroperitoneal masses had virtually disappeared and the pulmonary miliaria, which was still present, had regressed. This partial regression is still stable after two and a half years of observation.

This example shows that the clinical effect of the vaccination using the serum proteins can be maintained over a considerable period of time greater than 30 months.

Example 3: Results of the Administration of the Vaccine According to the Invention in a Patient Suffering from Colon Adenocarcinoma This patient presented a colon adenocarcinoma treated surgically and with adriamycin. At three years, pulmonary and hepatic metastases appeared, localized in a pulmonary lobe and a hepatic lobe, which allowed surgery of the lung and of the liver followed by chemotherapy. At 5 years, chemotherapy with gemcitabine, capecitabine and bevacizumab was introduced after reappearance of numerous hepatic and retroperitoneal lymph node metastases. Despite the chemotherapy, the disease continued to progress. Following halting of the chemotherapy subsequent to a pulmonary embolism, the tumor markers (ACE) strongly increased. The patient was treated by vaccination using the serum proteins (4 injections one week apart for the first month and then one injection/month) leading to a marked decrease in the level of marker. The markers then increased again 3 months later, suggesting vaccine escape by the tumor with a PET (positron emission tomography) identical to that done before the vaccination. Another preparation was thus produced using another serum sample and injected every three weeks, which resulted in a decrease in the markers below the normal values in less than three months. The PET reveals necroses of the hepatic metastases one year after the beginning of the immunotherapy.

In conclusion: the vaccine produced from blood inhibits cell proliferation in a first step, detectable by the cell proliferation markers, then exhibits a later effect, detectable by PET over a much longer period of time of several months to one year.

Example 4: Anti-Glioblastoma Serum Antibody Post-Vaccination with Vaccine Prepared from the Blood This patient was vaccinated 6 months after the discovery and surgical biopsy of a right temporal stage IV glioblastoma. The first-line treatment was a Stupp protocol (Stupp, R. et al., Radiotherapy plus Concomitant and Adjuvant Temozolomide for Glioblastoma, N Engl J Med 2005; 352:987-996) based on temodal alternating with radiotherapy. The vaccination using the serum proteins was carried out at a frequency of 4 injections, one week apart, for one month and then one injection per month through the survival time of the patient. The patient remained in complete remission for 10 months and in progress (RECIST criteria) for 2 months before dying. The presence of serum antibodies (IgG) was tested on sections of the tumor biopsy from the patient in order to see whether antibodies existed against the tumor cells.

Figure 3:
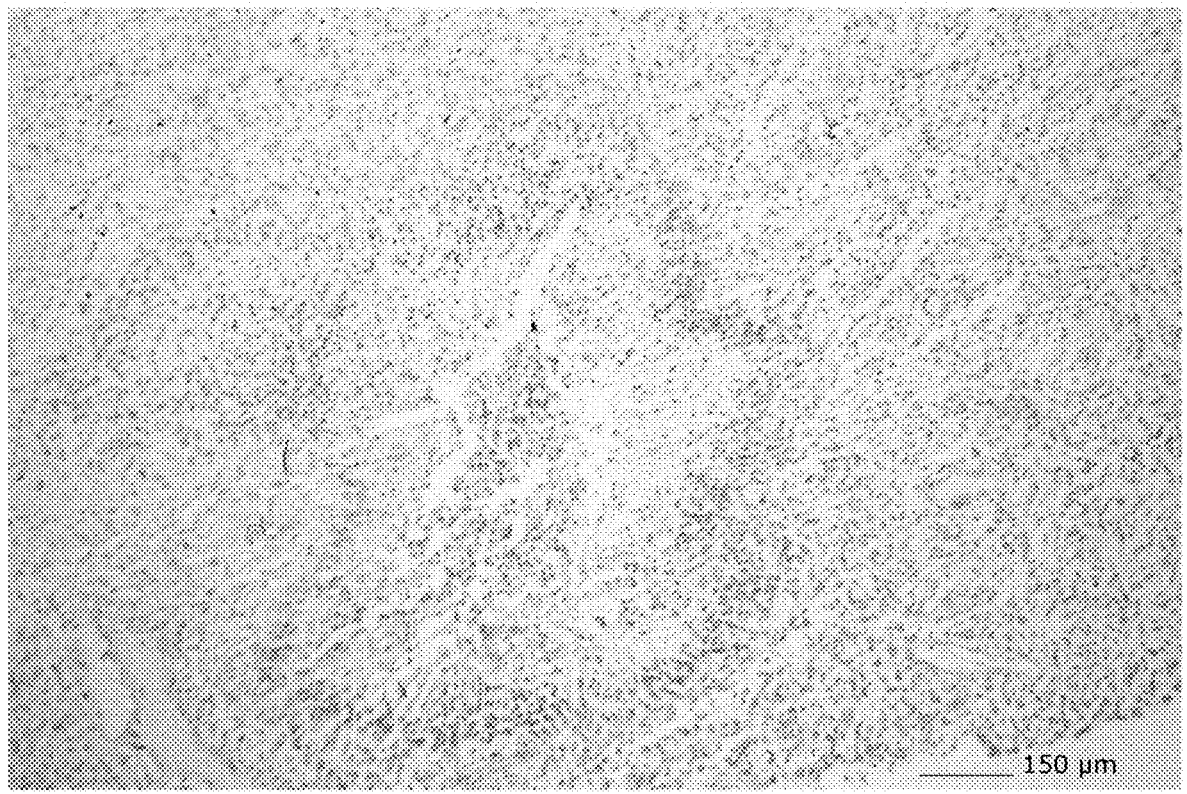
FIG. 3: Labeling of a glioblastoma section using anti-human IgGs showing that anti-tumor cell antibodies are present after vaccination, as shown by the peroxidase labeling (brown deposit).

Paraffin-embedded tissue sections 5 µm thick are used. They are deparaffinized in xylol and rehydrated in reducing solutions of ethanol. The endogenous peroxidases are inhibited with an $H_2O_2$ solution. The patient's serum was diluted to $1/100$ in a Hepes buffer and serves as primary antibody in a marker using a peroxidase-labeled anti-human IgG as secondary antibody. The peroxidase is then demonstrated using DAB (3,3'-diaminobenzidine) oxidized in the presence of hydrogen peroxide, said peroxidase producing a brown deposit insoluble in alcohol (FIG. 3). The negative control is a section treated under the same conditions without the primary antibody (diluted serum).

The labeling shows that a majority of the tumor cells are positive, but it should be noted that some of them are not. This suggests that the vaccine causes a reaction against the tumor cells and that the time period that exists between the biopsy and the production of the vaccine meant that not all the clones are represented in the vaccine.

This histology shows that the vaccination with the serum proteins triggers a humoral anti-tumor immune reaction.

Example 5: Difference Between the Percentage of Positive ELISPOTs Induced by the Vaccines Produced from a Tumor Biopsy and Those Produced from the Serum The CD8 stimulation induced by the vaccines produced from the blood or from a biopsy was compared. This was carried out on a series of patients with various cancerous pathological conditions for which a biopsy or a serum sample was taken depending on biopsy availability. It should be noted that the stimulation of cellular immunity detected by Elispot does not always correlate with the clinical result. Elispot does not detect all the CD8 stimulation states. The ELISPOT test was carried out in each patient at the fifth injection, that is to say three months after the first vaccination.

10 ml of blood are collected in a citrated tube and centrifuged, in ficoll 400, within 4 hours after taking the sample. The nucleated cells are then washed in RPMI medium and placed in culture in wells coated with vaccine proteins at a concentration of $2 \times 10^5$ cells/well. The vaccine proteins are obtained as previously described for carrying out the electrophoreses of the vaccines. 10 mg of protein-loaded powders are washed in 0.5 ml of 0.2 M NaCl. For coating the plates, the solution is brought back to 0.02 M. The cells are then cultured overnight in RPMI medium supplemented with 5% fetal calf serum at 37° C. in an incubator at 5% $CO_2$. The cells are then washed for 10 min in PBS containing 0.1% of tween20 detergent. The wells are then incubated for one hour in one ml of PBS with 0.1% of BSA and the peroxidase-labeled anti-gamma-interferon antibody diluted to $1/1000$. The peroxidase is then revealed as in example 4.

15 patients were vaccinated with vaccines produced from serum and 13 were vaccinated using vaccines produced from tumor biopsies. The ELISPOTs were carried out at the time of the $5^{th}$ injection, that is to say at the third month of vaccination. The negative control is the blood of a non-vaccinated patient having a tumor of the same type. 14/15 patients vaccinated using the serum have positive ELISPOTs, whereas only 6/13 of the patients vaccinated using the biopsies have a positive ELISPOT. This constitutes a statistically different difference.

In the light of these various results, given the differences in composition visible by electrophoresis and the results observed both clinically and biologically, there is a surprising effect of the vaccine obtained by means of this method.

The invention claimed is:

1. A method for treating a patient suffering from a cancer, said method comprising the following steps:
   a) extracting proteins contained in a serum or plasma sample obtained from a patient suffering from cancer;
   b) bringing the proteins extracted in step a) into contact with particles of hydroxyapatite and/or of tricalcium phosphate;
   c) suspending, in an injection liquid, the particles of hydroxyapatite and/or of tricalcium phosphate brought into contact with the proteins in step b);
   d) injecting the mixture obtained in step c) into the patient from whom the serum or plasma sample used in step a) was obtained.

2. The method as claimed in claim 1, wherein the patient is a human.

3. The method as claimed in claim 1, wherein the patient is a dog, a horse or a cat.

4. The method as claimed in claim 1, wherein the cancer is chosen from melanomas, carcinomas, adenocarcinomas, sarcomas, central nervous system tumors, leukemias, lymphomas and cancers of infectious origin.

5. The method as claimed in claim 1, wherein the cancer is chosen from the group consisting of osteosarcomas, B or T lymphomas, mammary tumors, melanomas, hemangiosarcomas, mastocytomas, fibrosarcomas, brain or central nervous system tumors, schwannomas, mesotheliomas, seminomas, teratomas and blastomas.

6. The method as claimed in claim 1, wherein the cancer is a glioblastoma, a sarcoma, a melanoma, a carcinoma or an adenocarcinoma.

7. The method as claimed in claim 1, wherein the cancer is a cancer exhibiting metastases.

* * * * *